(12) United States Patent
Hesketh et al.

(10) Patent No.: US 8,529,117 B2
(45) Date of Patent: Sep. 10, 2013

(54) MIXING APPARATUS FOR GASES

(75) Inventors: Trevor John Hesketh, Weybridge (GB);
Rune Peter Lindstedt, London (GB);
Ian Allan Beattie Reid, Southfields (GB)

(73) Assignee: Ineos Europe Limited, Hampshire (GB)

( * ) Notice: Subject to any disclaimer, the term of this patent is extended or adjusted under 35 U.S.C. 154(b) by 897 days.

(21) Appl. No.: 12/452,907

(22) PCT Filed: Sep. 22, 2008

(86) PCT No.: PCT/EP2008/062608
§ 371 (c)(1),
(2), (4) Date: Jan. 28, 2010

(87) PCT Pub. No.: WO2009/043751
PCT Pub. Date: Apr. 9, 2009

(65) Prior Publication Data
US 2010/0130802 A1 May 27, 2010

(30) Foreign Application Priority Data
Oct. 2, 2007 (EP) .................................. 07253896

(51) Int. Cl.
*B01F 3/02* (2006.01)
*B01F 5/04* (2006.01)

(52) U.S. Cl.
USPC ...................................... 366/178.1; 239/424

(58) Field of Classification Search
USPC .......... 366/178.1–178.2, 181.6, 173.1–173.2, 366/162.1, 167.1, 176.1, 177.1, 178.3; 239/423, 239/424; 48/189.4
See application file for complete search history.

(56) References Cited

U.S. PATENT DOCUMENTS

| | | | |
|---|---|---|---|
| 1,816,412 A * | 7/1931 | Tipton | 48/189.4 |
| 4,255,125 A | 3/1981 | Auclair et al. | |
| 4,360,497 A | 11/1982 | Casperson | |
| 4,408,890 A * | 10/1983 | Beckmann | 366/155.2 |

(Continued)

FOREIGN PATENT DOCUMENTS

| | | |
|---|---|---|
| DE | 3724344 | 7/1987 |
| DE | 19534107 | 3/1997 |

(Continued)

OTHER PUBLICATIONS

PCT International Preliminary Report on Patentability; PCT International Application No. PCT/EP2008/062608; International Filing Date Sep. 22, 2008 (7 pgs).

(Continued)

*Primary Examiner* — Charles E Cooley
(74) *Attorney, Agent, or Firm* — Nixon & Vanderhye

(57) ABSTRACT

Apparatus for mixing of a first gas and a second gas, including (i) a linear first tube for supply of the first gas, the first tube having an inlet for the first gas at an upstream end and tapering to form a nozzle at a downstream end, and (ii) a linear second tube for supply of the second gas. The second tube has an inlet for the second gas at an upstream end, a first portion which forms an annulus around the outer surface of the first tube upstream of the nozzle, and a second portion which forms a sheath around the nozzle of the first tube and which forms an area of expanded cross-section compared to the annulus.

15 Claims, 5 Drawing Sheets

(56) References Cited

U.S. PATENT DOCUMENTS

| | | | |
|---|---|---|---|
| 4,769,506 A | 9/1988 | Kosters | |
| 4,795,547 A | 1/1989 | Barnes | |
| 6,736,960 B1 | 5/2004 | Chen et al. | |
| 7,182,282 B2 * | 2/2007 | Bedetti | 239/654 |
| 2002/0050097 A1 | 5/2002 | Fournier et al. | |
| 2008/0074944 A1 * | 3/2008 | Blechschmitt et al. | 366/101 |
| 2008/0267006 A1 * | 10/2008 | Moreira Campos | 366/165.1 |
| 2010/0130802 A1 * | 5/2010 | Hesketh et al. | 585/520 |
| 2011/0259971 A1 * | 10/2011 | Askin et al. | 239/8 |
| 2012/0314526 A1 * | 12/2012 | Shah et al. | 366/101 |

FOREIGN PATENT DOCUMENTS

| | | | |
|---|---|---|---|
| DE | 29617621 | | 8/1997 |
| EP | 0 239 171 A2 | | 9/1987 |
| EP | 0 332 289 | | 9/1989 |
| GB | 672446 | | 5/1952 |
| GB | 1281414 | | 7/1972 |
| GB | 1 407 281 | | 9/1975 |
| GB | 1459793 | | 12/1976 |
| JP | 59183820 A | * | 10/1984 |
| JP | 63216973 | | 9/1988 |
| WO | WO 02/087776 A1 | | 11/2002 |
| WO | WO 2004/004878 A1 | | 1/2004 |
| WO | WO 2004/074222 A1 | | 9/2004 |
| WO | WO 2007/045457 A1 | | 4/2007 |

OTHER PUBLICATIONS

Ishikawa, et al; "An experimental study on the performance of mixed-flow-type conical walled annular diffusers"; *Coll. Sci. Tech., Meijo Univ.*, Nagoya, Japan; 54(507), 3157-64 (1988).

* cited by examiner

MIXING APPARATUS FOR GASES

This application is the U.S. national phase of International Application No. PCT/EP2008/062608 filed 22 Sep. 2008 which designated the U.S. and claims priority to European Patent Application No. 07253896.0 filed 2 Oct. 2007, the entire contents of each of which are hereby incorporated by reference.

The present invention relates to an apparatus for mixing of a first gas and a second gas, and in particular of a hydrocarbon-containing gas and an oxygen-containing gas.

BACKGROUND OF THE INVENTION

The mixing of hydrocarbon and oxygen-containing gases is required in many known processes. In many of these processes, the formed mixture may be in the flammable regime, by which is meant that the mixture, if it comes into contact with a suitable ignition source will combust. The flammability of fuel-oxygen mixtures, even within the flammable range can also vary. Thus, fuel-oxygen mixtures which are close to the stoichiometric composition possess higher burn rates than those mixtures found close to the flammable limits or are predominantly fuel rich. In particular, such mixtures are easily ignited and produce more stable flames that will rapidly propagate through a flammable mixture. These near stoichiometric mixtures can also lead to the generation of significant pressures and temperatures following ignition, and flames may only be extinguished by withdrawing a reactant.

It requires a finite time to mix fuel and oxygen and a wide range of mixtures may be formed during the mixing process. Thus, it is desirable to minimise the presence of more reactive, near stoichiometric, flammable mixtures even in mixtures where the nominal mixed composition is outside of the flammable regime or within the flammable range but with relatively low burn rate properties.

A number of other factors can increase the upper flammable limit, reducing the amount of oxygen required to sustain combustion, and expanding the range of potentially flammable gas mixtures, including, for example, the use of pure oxygen rather than air, increased temperature and pressure.

Rapid and efficient mixing is thus desired, and the object of an efficient mixer is to minimise the volume of highly reactive oxygen rich gas mixtures.

The auto-thermal cracking process is a known process for the production of olefins, in which a hydrocarbon and an oxygen-containing gas are mixed and subsequently contacted with a catalyst. The hydrocarbon is partially combusted on the catalyst, and the heat produced is used to drive the dehydrogenation of the hydrocarbon feed into olefins. An example of such a process is described in EP-A-0 332 289.

It is desired that the hydrocarbon and the oxygen-containing gas are uniformly mixed and preheated prior to contacting the catalyst. However, the mixture of hydrocarbon and oxygen-containing gas for the autothermal cracking process is flammable. Thus, it is desired to reduce the residence time in the reactor of the mixed gas stream, and in particular, it is usually desired, especially as pressure is increased, to mix the hydrocarbon and the oxygen-containing gas and contact them with the catalyst within significantly less than 1 second, usually significantly less than 100 ms.

WO 2004/074222 describes a reactor for the autothermal cracking of olefins, and in particular which provides a reactor design that enables an auto-thermal cracking process to be conducted wherein the gaseous reactants are preheated separately, mixed and subsequently contacted with a suitable catalyst. WO 2004/074222 describes two specific configurations for mixing first and second gaseous reactants (preferably hydrocarbon and oxygen-containing gases) in a uniform manner. One of these designs involves a tube-in-tube configuration with a plurality of conduits in each of which is provided an injection tube terminating in a nozzle through which the first gas exits into the second gas in the conduit.

SUMMARY OF THE INVENTION

It has now been found that a specific design provides yet further improvements in the mixing of a first gas and a second gas.

In particular, the present invention provides a mixing apparatus for mixing a first gas and a second gas, which mixing apparatus comprises:
i) a linear first tube for supply of the first gas, said first tube comprising an inlet for the first gas at an upstream end and tapering to form a nozzle at a downstream end, said nozzle having an opening of internal area of less than 10 mm$^2$ at the outlet for the first gas and providing a pressure drop in the supply of the first gas through said first tube, and
ii) a linear second tube for supply of the second gas, said second tube comprising an inlet for the second gas at an upstream end, a first portion which forms an annulus around the outer surface of the first tube upstream of the nozzle, which annulus has a length of 5 to 50 mm and a cross-section area of 2 to 10 times the area of the opening of the nozzle and which acts to provide a pressure drop in the supply of the second gas through said second tube, and a second portion which forms a sheath around the nozzle of the first tube and which forms an area of expanded cross-section compared to the annulus,
and wherein:
a) the nozzle and annulus are arranged such that the pressure drops caused in the supply of the first and second gases are in a ratio of 2:1 to 1:2,
b) the angle of the external taper of the nozzle is less than 12° compared to the longitudinal axis of the first tube, and
c) any change in diameter of second tube in the second portion is less than 12° compared to the longitudinal axis of the second tube.

Typically, the mixing apparatus comprises a plurality of linear first and second tubes as defined herein and provided in parallel, preferably at least 100, more preferably at least 500, and most preferably at least 1000 first and second tubes (in total). The mixing apparatus usually comprises less than 10000 first and second tubes (in total). Each linear first tube and associated linear second tube may be considered as a "pair". The pairs are preferably evenly spaced from each other, most preferably such that the outlets of the second linear tubes have a regular pitch, preferably a square pitch or a triangular pitch. In use, this provides an even distribution of mixed gas downstream of the first and second tubes.

In use, the mixing apparatus according to the present invention provides a number of advantages. Firstly, the relatively small dimensions of each of the linear first and second tubes provides more efficient mixing than larger designs. The mixing also occurs in an essentially parallel manner at the exit of the linear first tube, and the relatively small dimensions of the nozzle and annulus avoids swirling motion in the mixed gases. Swirling gases can lead to stagnant or partially stagnant zones and increase overall residence times.

Thus, the present invention provides a design of mixing apparatus which provides rapid and uniform mixing of the gases whilst minimising turbulence and instabilities in the mixing region.

Without wishing to be bound by theory, it is believed that the restriction on angles of tapers of nozzles and changes in the dimensions of tubes is important to maintain smooth flow. The restriction on the changes in the tube dimensions specifically excludes relatively sharp changes, including "step" changes, which have been found to cause flow detachment and oscillations in the flow.

In particular it has been established through real time CFD modelling that flow detachment or flow recirculation may be a source of flow instability in the device. In certain cases this may lead to substantial changes to mixture composition, leading to rapid oscillation between fuel rich and fuel lean compositions which are clearly undesirable as this may lead to short lived high gas temperatures or reaction extinction.

In the preferred embodiment with multiple tubes, the use of a large number of tubes of small dimensions rather than a smaller number of large tubes allows the mixing of relatively large volumes of flammable gases whilst reducing the inventory of potentially flammable mixture in each tube, which limits the potential magnitude of an in-tube explosion. The tube dimensions of the present invention also ensure high linear flow rates per tube, which can "blow" mild flame propagation events out of the tubes preventing back-flow of any flame.

Part (i) of the mixing apparatus of the present invention comprises a linear first tube for supply of the first gas, said first tube comprising an inlet for the first gas at an upstream end and tapering to form a nozzle at a downstream end, said nozzle having an opening of internal area of less than 10 mm$^2$ at the outlet for the first gas and providing a pressure drop in the supply of the first gas through said first tube.

The key features of the nozzle are that the relatively small nozzle opening and the angle of the external taper of the nozzle being less than 12° compared to the longitudinal axis of the first tube.

Preferably, the nozzle comprises only one opening and which is provided such that the gas flowing through the linear first tube exits axially from the end of the linear first tube.

More preferably, the angle of the external taper of the nozzle is less than 7° compared to the longitudinal axis of the first tube.

The internal area of the opening of the nozzle is preferably less than 5 mm$^2$, for example 0.5 to 5 mm$^2$, most preferably 1 to 3 mm$^2$. (The internal area of 0.5 to 5 mm$^2$ corresponds to a circle of approximately 0.8 to 2.5 mm diameter.) The internal area of the opening of the nozzle should be less than the internal cross-sectional area of the linear first tube other than at the nozzle. The relatively small nozzle opening thus sets the pressure drop in the linear first tube. The pressure drop is typically in the range 0.1 to 4 bar (10 to 400 kPa), preferably 0.3 to 3 bar (30 to 300 kPa).

Other than the fact that to allow the linear first tube to reside inside the linear second tube the external size/diameter of the linear first tube must be less than the internal diameter of the linear second tube at any particular point, the exact external diameter of the linear first tube is not critical to the invention. With the exception of the nozzle region i.e. where the linear first tube externally tapers at the nozzle, usually the linear first tube has an external diameter of between 2.0 to 10.0 mm. The external diameter may vary along the length of the linear first tube (other than at the nozzle). Preferably any changes in external diameter of the linear first tube are at an angle of less than 12° compared to the longitudinal axis of the linear first tube, more preferably, less than 7°.

At the exit of the nozzle the external diameter is as close to the internal diameter as possible i.e. the thickness of the tube is as small as possible at this point. In practical terms, at the exit there is likely to be a tube thickness of 0.2 to 0.5 mm i.e. an external diameter of 0.4 to 1.0 mm more than the internal diameter of the opening of the nozzle.

The internal diameter may also vary along the length of the linear first tube other than at the nozzle. The tube need not taper internally so that the opening of internal area of less than 10 mm$^2$ occurs only at the very end of the linear first tube corresponding to the outlet for the first gas, and may have a bore which has a short length (e.g. 1 to 2 mm) with an internal area corresponding to the area of the opening, and then widen upstream. Either way, because the bore of the linear first tube upstream of this section has a cross-sectional area which is greater than the area at the tip, the flow of gas through the linear first tube is being squeezed into a smaller diameter at the nozzle, and flow detachment is less of a concern. Therefore the relatively gentle slopes of other surfaces of the present invention are not required within the linear first tube, although it is generally preferred to minimise, preferably avoid, step changes in internal diameter and to minimise any angles at changes in the internal diameter.

Part (ii) of the mixing apparatus of the present invention comprises a linear second tube for supply of the second gas, which second tube comprises an inlet for the second gas at an upstream end, a first portion which forms an annulus around the outer surface of the first tube upstream of the nozzle, which annulus has a length of 5 to 50 mm and a cross-section area of 2 to 10 times the area of the opening of the nozzle and which acts to provide a pressure drop in the supply of the second gas through said second tube, and a second portion which forms a sheath around the nozzle of the first tube and which forms an area of expanded cross-section compared to the annulus.

The key features of the linear second tube are the first portion which forms an annulus around the outer surface of the first tube upstream of the nozzle, which annulus cross-section has a length of 5 to 50 mm and a cross-section area of 2 to 10 times the area of the opening of the nozzle, the second portion which forms a sheath around the nozzle of the first tube and which forms an area of expanded cross-section compared to the annulus, and that any change in diameter of the second tube in the second portion is less than 12° compared to the longitudinal axis of the second tube.

By "any change in diameter of the (first/second) tube is less than (X)° compared to the longitudinal axis of the (first/second) tube", as used herein is meant that the changes in the relevant diameter occur due to a slope or taper at less than the defined angle (rather than higher angles or steps, for example).

More preferably, any change in diameter of the second tube in the second portion is less than 7° compared to the longitudinal axis of the second tube.

The annulus is formed by a length of relatively narrow cross-section immediately upstream of the nozzle. For avoidance of doubt, "annulus" as used herein refers to a volume between the external surface of the linear first tube and the internal surface of the linear second tube. The annulus is of low cross-section area compared to upstream and downstream volumes in fluid communication therewith (e.g. between the linear second tube and any surfaces inside the linear second tube). The cross-section of the annulus is the area between the external surface of the linear first tube and the internal surface of the linear second tube, which is usually, and preferably, a ring-shaped area of constant cross-section along the length of the annulus. Where the cross-section varies along the length of the annulus, reference to the cross-section area is considered to be the average cross-section area along the length of the annulus. In this scenario, preferably the maximum annulus cross-section is less than 10 times the area of the opening of the nozzle at any point along the annulus length.

Ideally, the linear first tube and the linear second tube are concentric, at least within the annulus region. However, it will be readily apparent that an off-set from such a concentric configuration may be present. In general, such an off-set may be tolerated as long as the required relative overall pressure drops are obtained in each tube pair.

The annulus is preferably of a length of 5-30 mm, preferably 10 to 25 mm.

Preferably the annulus cross-section is 3-8 times, more preferably 4-6 times the area of the opening of the nozzle. In absolute terms, the annulus cross-section area is typically less than 60 mm$^2$, for example 5-60 mm$^2$, more preferably 5 to 25 mm$^2$.

The annulus sets the pressure drop in the linear second tube. The pressure drop is typically in the range 0.1 to 4 bar (10 to 400 kPa), preferably 0.3 to 3 bar (30 to 300 kPa).

The nozzle and annulus are arranged such that the pressure drops caused in the supply of the first and second gases are in a ratio of 2:1 to 1:2. Preferably, a slightly larger pressure drop is provided in the linear second tube, for example the pressure drops caused in the supply of the first and second gases are in a ratio of 1:1 to 1:1.5, more preferably 1:1 to 1:1.3. This has been found to provide further benefits in avoiding pressure fluctuations.

Upstream of the annulus, the linear second tube usually has a wider internal cross-section compared to the portion at the annulus, the cross-section narrowing in the downstream direction, usually by narrowing of the internal diameter of the second tube, to the diameter required for the annulus. Preferably all such changes occur at an angle of less than 12°, more preferably less than 7°, (as used herein, all such angles are compared to the longitudinal axis of the respective tube unless stated otherwise). In the second portion, it is possible to expand or contract the internal diameter of the linear second tube, as long as the other requirements on angles and expansion are met, but preferably the second portion is of constant internal diameter, and the external taper (narrowing) of the nozzle causes the required area of expanded cross-section compared to the annulus.

Preferably any change in the internal diameter of the linear second tube downstream of the nozzle is also at angle of less than 12°, more preferably less than 7°.

The length of the linear first tube within the linear second tube is usually between 5-50 mm, preferably between 10-40 mm, and most preferably between 25-35 mm e.g. 30 mm.

The total length of the second tube is not critical, although it is preferred it extends beyond the exit/opening at the nozzle by a length of at least 10 times its internal diameter to ensure that good mixing is obtained before the mixed gas exits the second tube, preferably in the range of 20 to 40 times its internal diameter.

Suitably, the second tube extends beyond the exit at the nozzle with an internal diameter in the range 5 to 15 mm. Most preferably, therefore, the length of second tube beyond the nozzle is in the range 50 to 500 mm and a total length in the range 55 to 550 mm (length of section into which linear first tube protrudes plus length of second tube beyond nozzle).

Preferably the linear first and second tubes are formed of a suitable metal or alloy e.g. steel. Where pure oxygen is employed as a gaseous reactant it may be necessary to make or coat some or all of any part of the mixing apparatus that may contact the oxygen from/with an alloy that resists reaction with oxygen. Reaction with oxygen is more likely when the temperature of the oxygen is high and/or the oxygen is at high velocity. Suitable alloys include alloys of copper and nickel, such as those in the MONEL™ range.

The mixing apparatus is advantageously employed as part of a reactor to mix and react the first and second gases. Thus, in another embodiment the present invention provides a reactor for the mixing and reaction of a first gas and a second gas, which reactor comprises a mixing zone comprising the mixing apparatus described herein and a reaction zone downstream of the mixing zone.

In another embodiment, the present invention provides a process for the mixing and reaction of a first gas and a second gas, which process comprises feeding said first gas and said second gas to, respectively, one or more linear first tubes and one or more linear second tubes in a mixing apparatus as described herein and subsequently passing the gaseous mixture obtained to a reaction zone downstream of the mixing zone.

The first gas and the second gas may be any suitable gases, but preferably the first gas is an oxygen-containing gas and the second gas is a paraffinic hydrocarbon-containing gas.

Preferably a filter and/or coalescer may be provided on the first gas and/or second gas supplies to remove fine particles or liquid droplets that may be present in said streams.

In a most preferred embodiment, the present invention provides a process for the production of one or more olefins, said process comprising mixing an oxygen containing gas and a paraffinic hydrocarbon-containing gas by passing the oxygen-containing gas as the first gas and the paraffinic hydrocarbon-containing gas the second gas to a mixing apparatus as described herein, passing the gaseous mixture obtained to a reaction zone via a porous resistance zone, and partially combusting in the reaction zone the gaseous mixture, preferably in the presence of a catalyst which is capable of supporting combustion beyond the fuel rich limit of flammability, to produce the one or more olefins.

Other than the specific features of the mixing apparatus of the present invention, the preferred features of the process according to this embodiment and the reactor for performing the process, such as upstream reactant supply, downstream resistance zone, catalyst zone and so on are as described in WO 2004/074222.

For example, the plurality of linear first and second tubes usually comprises at least 500, most preferably at least 1000 first and second tubes (in total) per metre squared of the transverse cross section of the reaction zone.

Similarly, the first and second gases can be supplied by any suitable means, but preferably utilise a first and second supply means, the first supply means comprising at least one first inlet for supplying a first gas to at least one first manifold and a plurality of linear first tubes exiting said first manifold for delivery of the first gas, and the second supply means comprising at least one second inlet for supplying a second gas to at least one second manifold and a plurality of linear second tubes exiting said second manifold for delivery of the second gas, wherein the second manifold is positioned downstream of the first manifold with respect to the flow of the first gas, and wherein each linear second tube comprises an upstream end exiting the second manifold and a downstream end in fluid communication with the resistance zone and wherein the linear first tubes exiting the first manifold are arranged such that they extend through the second manifold and project axially into the upstream ends of the linear second tubes.

The resistance zone is porous. The permeability of the porous resistance zone ensures dispersion of the fluid reactants as they pass through the zone. The fluids move through a network of channels laterally as well as axially (axially being the general direction of flow of the reactants through the resistance zone), and leave the resistance zone substantially uniformly distributed over the cross-sectional area of the resistance zone.

The resistance zone may be formed of a porous metal structure, but preferably the porous material is a non metal e.g. a ceramic material. Suitable ceramic materials include lithium aluminium silicate (LAS), alumina ($\alpha$-$Al_2O_3$), yttria stabilised zirconia, alumina titanate, niascon, and calcium zirconyl phosphate. A preferred porous material is alpha alumina.

When a catalyst is employed suitably the catalyst is a supported platinum group metal. Preferably, the metal is either platinum or palladium, or a mixture thereof. Although a wide range of support materials are available, it is preferred to use alumina as the support. The support material may be in the form of spheres, other granular shapes or ceramic foams. Preferably, the support is a monolith which is a continuous multichannel ceramic structure, frequently of a honeycomb appearance. A preferred support for the catalytically active metals is a gamma alumina. The support is loaded with a mixture of platinum and palladium by conventional methods well known to those skilled in the art. The resulting compound is then heat treated to 1200° C. before use. catalyst promoters may also be loaded onto the support. Suitable promoters include copper and tin.

The catalyst is usually held in place in the reactor in a suitable holder, such as a catalyst basket. Preferably, to prevent gas by-passing the catalyst between the catalyst and the holder, any space between the catalyst and the holder is filled with a suitable sealing material. Suitable sealing materials include man made mineral wools e.g. ceramic wool, which can be wrapped around the edges of the catalyst in the holder. In addition the catalyst may be coated around the edge with a material similar to the main catalyst support material, such as alumina, to aid this sealing.

The reactor may comprise a product cooling zone downstream of the reaction zone, such that the gaseous products can be cooled upon exiting the reaction zone. The product cooling zone may be provided by one or more injection nozzles that are capable of injecting a condensate into the product stream exiting the reaction zone.

In the process for the production of a mono-olefin from a feedstock comprising a gaseous paraffinic hydrocarbon, the paraffinic hydrocarbon may suitably be ethane, propane or butane. The paraffinic hydrocarbon may be substantially pure or may be in admixture with other hydrocarbons and optionally other materials, for example methane, nitrogen, carbon monoxide, carbon dioxide, steam or hydrogen. A paraffinic hydrocarbon-containing fraction such as naphtha, gas oil, vacuum gas oil, or mixtures thereof, may be employed. A suitable feedstock is a mixture of gaseous paraffinic hydrocarbons, principally comprising ethane, resulting from the separation of methane from natural gas. A preferred feedstock is a paraffinic hydrocarbon principally comprising ethane which provides a product principally comprising ethylene as the mono-olefin.

As the oxygen-containing gas there may suitably be used either oxygen or air. It is preferred to use oxygen, optionally diluted with an inert gas, for example nitrogen. The ratio of the gaseous paraffinic hydrocarbon to the oxygen-containing gas mixture is usually from 5 to 20 times the stoichiometric ratio of hydrocarbon to oxygen-containing gas for complete combustion to carbon dioxide and water. The preferred composition is from 5 to 10 times the stoichiometric ratio of hydrocarbon to oxygen-containing gas.

Although the mixing apparatus (and reactor) can be used at any pressure it is particularly useful at elevated pressure. The pressure is preferably between 1-5 MPa, most preferably between 1-4 MPa, and advantageously between 1.5-3.5 MPa.

The oxygen containing gas may be fed at ambient temperature, but is usually preheated to 50 to 150° C., preferably 80-120° C. e.g. 100° C. The oxygen containing gas is injected into the linear first tubes at a velocity to prevent the possibility of a flame stabilizing on the exits of the nozzles. The linear exit velocity is typically greater than 30 m/s, preferably greater than 50 m/s, and advantageously greater than 70 m/s.

The gaseous paraffinic hydrocarbon is usually preheated to 100 to 400° C., preferably 150-350° C. e.g. 300° C. and passed into the linear second tubes. The gaseous paraffinic hydrocarbon enters the tubes at a linear velocity typically greater than 5 m/s, preferably greater than 15 m/s, and advantageously greater than 20 m/s.

The linear velocity of the oxygen containing gas exiting the nozzles and the linear velocity of the gaseous paraffinic hydrocarbon at the (external to the) nozzles preferably has the ratio of at least 1.5:1, preferably at least 3:1 and most preferably less than 6:1, such as 4:1.

The temperature of the gaseous mixture is usually between 100 to 400° C., preferably 100 to 300° C. e.g. 200° C.

The formed gaseous mixture is usually passed to the resistance zone at a mean cross-section velocity between 1.0-10.0 m/s, preferably between 2.0-6.0 m/s and most preferably between 2.5-3.5 m/s.

The gaseous mixture is usually passed to the reaction zone at a velocity between 1.0-10.0 m/s, preferably between 2.0-6.0 m/s and most preferably between 2.5-3.5 m/s.

The pressure drop through the resistance zone is typically between 0.01-0.5 bar (1-50 kPa), and preferably between 0.05-0.25 bar (5 to 25 kPa) e.g. 0.15 bar (15 kPa).

The temperature in the reaction zone is usually greater than 650° C., typically greater than 750° C., and preferably greater than 800° C. The upper temperature limit may suitably be up to 1200° C., for example up to 1100° C.

The products exit the reaction zone at a temperature greater than 800° C. e.g. greater than 900° C., and at a pressure usually between 1-5 MPa, preferably between 1-4 MPa, and advantageously between 1.5-3.5 MPa.

Preferably the products are rapidly cooled in a product cooling zone. This ensures a high olefinic yield because the product cooling step slows down the rate of reaction in the gaseous product stream thus preventing further reactions taking place.

Advantageously the gaseous product stream is cooled by injecting a condensate into the gaseous product stream, preferably at multiple points, such that the vaporisation of the condensate cools the gaseous product stream.

The condensate may be a gas or a liquid. When the condensate is gas it is preferably an inert gas. Preferably the condensate is a liquid e.g. water.

Injecting the condensate at high pressure and high temperature ensures that a large proportion of the condensate instantaneously vaporizes at the reactor pressure and therefore provides a very rapid temperature drop in the gaseous product stream. Consequently the condensate, such as water, is usually injected at a pressure higher than the pressure of the gaseous product stream, such as 10 MPa and is usually injected at a temperature of between 100-400° C. and preferably between 200-350° C. e.g. 300° C.

Preferably the temperature of the gaseous product stream is reduced to 800° C. preferably to 600° C. within 60 mS preferably 40 mS and advantageously 20 mS from exiting the reaction zone.

The linear first and second tubes may be produced by conventional techniques, with surface finish determined by the technique used, such as standard machining, ground finish and reaming.

In a most preferred embodiment, the surface finish at least in the annulus region, and preferably at least in the areas of the first and second tubes immediately prior to the annulus, in the annulus itself and in the sheath/nozzle region downstream of the annulus is controlled at least to grade N6 (as defined by ISO 4287:2000 and which is equivalent to a roughness average (Ra) of 0.8 microns, as measured according to ASME B46.1 (American Society of Mechanical Engineers)).

Especially in a mixing apparatus with a plurality of tubes, and more especially for use at industrial scale (e.g. greater than 1000 first and second tubes (in total)) each combination (pair) of a linear first tube and a linear second tube in the mixing apparatus is preferably a "matched pair". By this is meant that each combination of linear first tube and linear second tube has been specifically selected or approved by an experimental test to ensure the required mixing characteristics prior to use in the mixing apparatus according to the present invention. Whilst modelling is able to predict mixing characteristics for "perfect" tubes, the tolerances required for the process of the present invention are relatively tight, and it has been found to be especially advantageous to ensure that all combinations of linear first tube and linear second tube not only provide the required individual mixing characteristics but also acceptable mixing characteristics relative to all other pairs of tubes prior to use in an actual mixing apparatus with said plurality of other combinations.

This may be done by any suitable technique. One particular example is to individually place a linear first tube and a linear second tube in the correct relative configuration to each other in a test apparatus, and pass pressurised gases at set flow rates through each tube individually whilst measuring the pressure drops in each. The test may be repeated for each tube combination (or may be done in parallel on a number of tube combinations) and only those meeting the required tolerances selected. In a variation of the above, which may alternatively be used, each first tube is tested against a reference second tube and each second tube is tested against a reference first tube, and the results used to determine acceptable pairings.

BRIEF DESCRIPTION OF THE DRAWINGS

The present invention will now be illustrated with the aid of FIGS. 1 to 5 and the Examples, wherein.

DETAILED DESCRIPTION OF THE INVENTION

Figure 1:
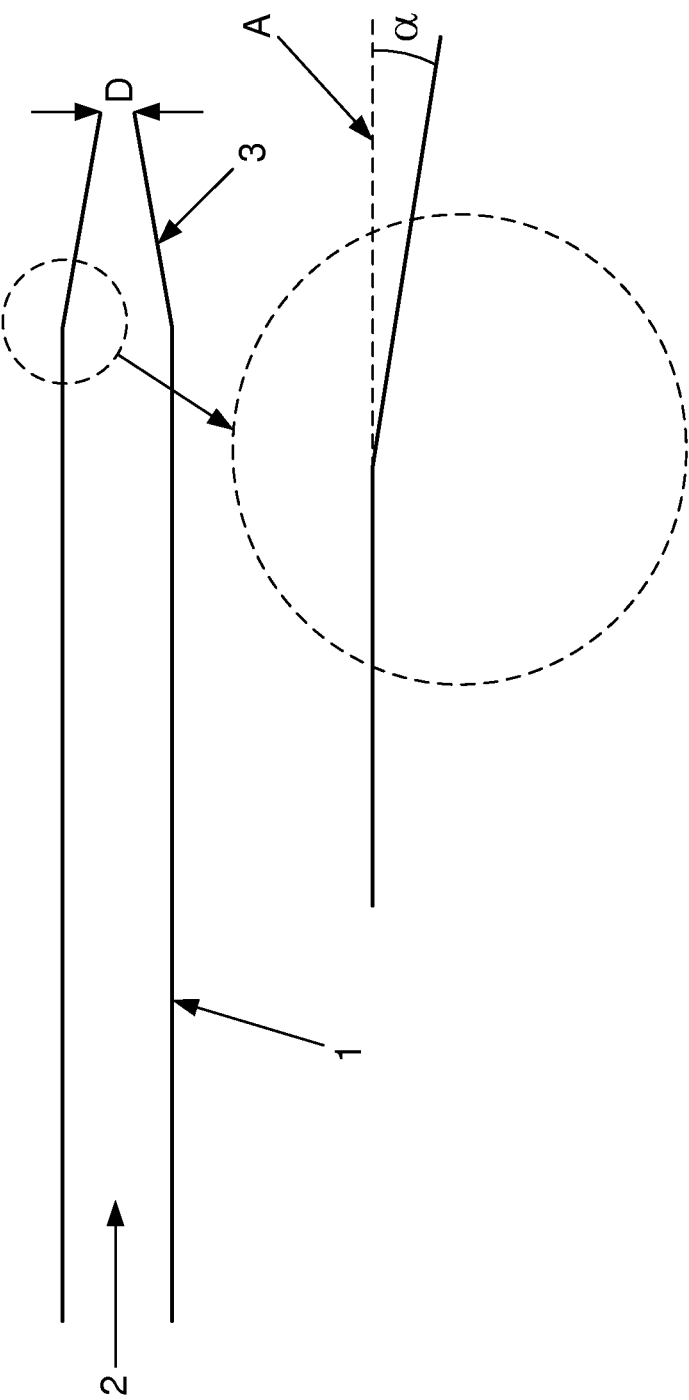
FIG. 1 represents in schematic form a linear first tube.
Figure 2:
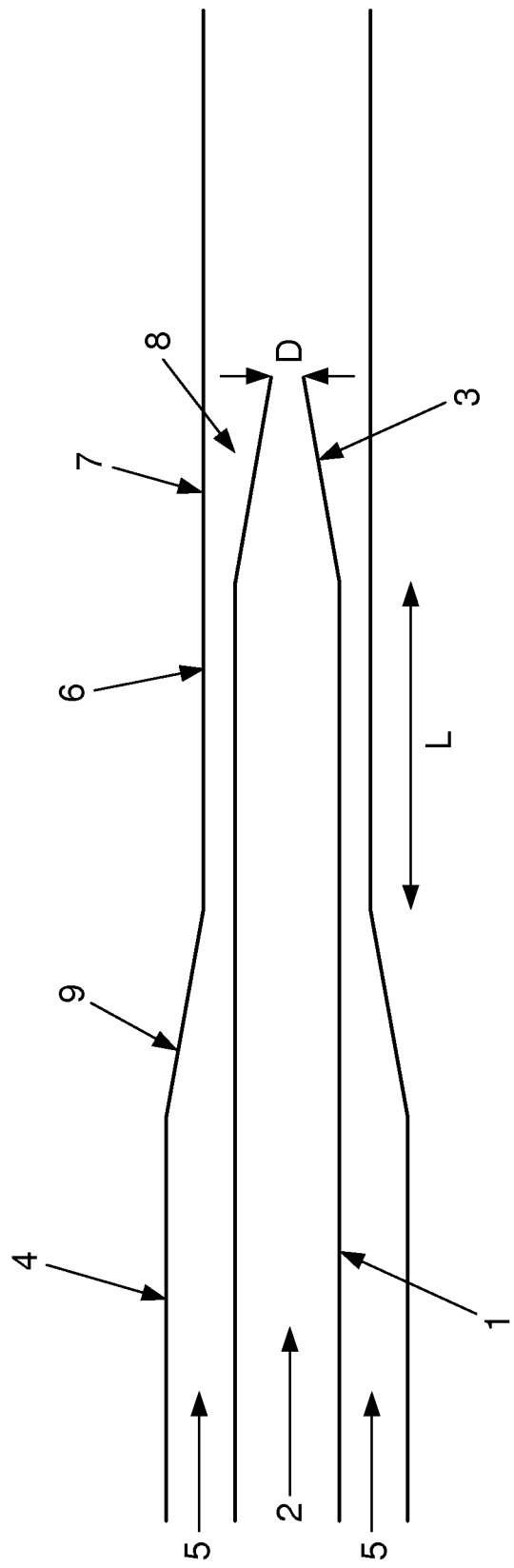
FIG. 2 represents in schematic form a mixing apparatus according to the present invention.

In particular, with regards to FIGS. 1 and 2, in FIG. 1 there is shown a linear first tube (1) for supply of the first gas, said first tube comprising an inlet (2) for the first gas at an upstream end and tapering to form a nozzle (3) at a downstream end. The angle of the external taper of the nozzle is less than 12° compared to the longitudinal axis of the first tube, this angle being shown in the expanded bubble by the angle α (the dashed line A represents a theoretical extension of the wall of the linear first tube prior to the nozzle, which line is parallel to the longitudinal axis of the linear first tube). The nozzle has an internal area at the opening (shown by its diameter D) of less than 10 mm$^2$ and providing a pressure drop in the supply of the first gas through said first tube.

In FIG. 2 there is shown a linear first tube (1) for supply of the first gas as in FIG. 1. FIG. 2 shows the linear first tube in place within a linear second tube (4) for supply of the second gas which second tube comprises an inlet (5) for the second gas at an upstream end, a first portion (6) which forms an annulus around the outer surface of the first tube upstream of the nozzle, which annulus has a length (L) of 5 to 50 mm and a cross-section area of 2 to 10 times the area of the opening of the nozzle, and which acts to provide a pressure drop in the supply of the second gas through said second tube, and a second portion (7) which forms a sheath around the nozzle (3) of the first tube and which forms an area of expanded cross-section (8) compared to the annulus.

Upstream of the annulus, the linear second tube has a wider internal diameter compared to the portion at the annulus (and providing an area between the external surface of the linear first tube and the internal surface of the linear second tube of wider cross-section than at the annulus), the linear second tube narrowing in the downstream direction at an angle of less than 12° (shown by 9), to the diameter required for the annulus.

EXAMPLES

Acoustic measurements have been made on a design according to the present invention and a similar design but with a "step" in the internal diameter of the linear second tube, and without the 12° limitation on the nozzle according to the present invention.

The acoustic measurements were performed using an apparatus in which were held, in the required configuration for mixing, linear first and second tubes. Air was then passed at flow rates typical for the respective oxygen and hydrocarbon gases conventionally used through the respective first and second linear tubes and a microphone with a PC based sound recorder was used to record the sound and convert this to an acoustic spectrum.

The details of the respective configurations are given in Table 1. In particular for the Comparative Example the second tube included a 1 mm step in the wall 10 mm upstream of the nozzle opening and the nozzle of the linear first tube had an external taper of 16°. In the Example of the present invention (Example 1) the general structure was as shown in FIG. 2, and in particular the dimensions were changed such that no step was present (sloped changes in diameter), and the external taper of the nozzle was reduced to 7°. This configuration results in respective pressure drops in the nozzle and annulus in a ratio of approximately 1:1.3.

TABLE 1

|  | Annulus external diameter | Annulus internal diameter | Annulus cross-section | Nominal Annulus length | Nozzle diameter | Nozzle opening | Nozzle taper |
|---|---|---|---|---|---|---|---|
| Comparative Example | 6.7 mm | 5.8 mm | 8.8 mm$^2$ | 4 mm | 1.9 mm | 2.8 mm$^2$ | 16° |
| Example 1 | 8.00 mm | 7.45 mm | 6.7 mm$^2$ | 25 mm | 1.70 mm | 2.3 mm$^2$ | 7° |

For both configurations, air was passed through the linear first tube at a linear velocity of 90 m/s and through the linear second tube at a linear velocity, measured in the annulus, of 30 m/s (said velocities being typical of expected operation).

Figure 3:
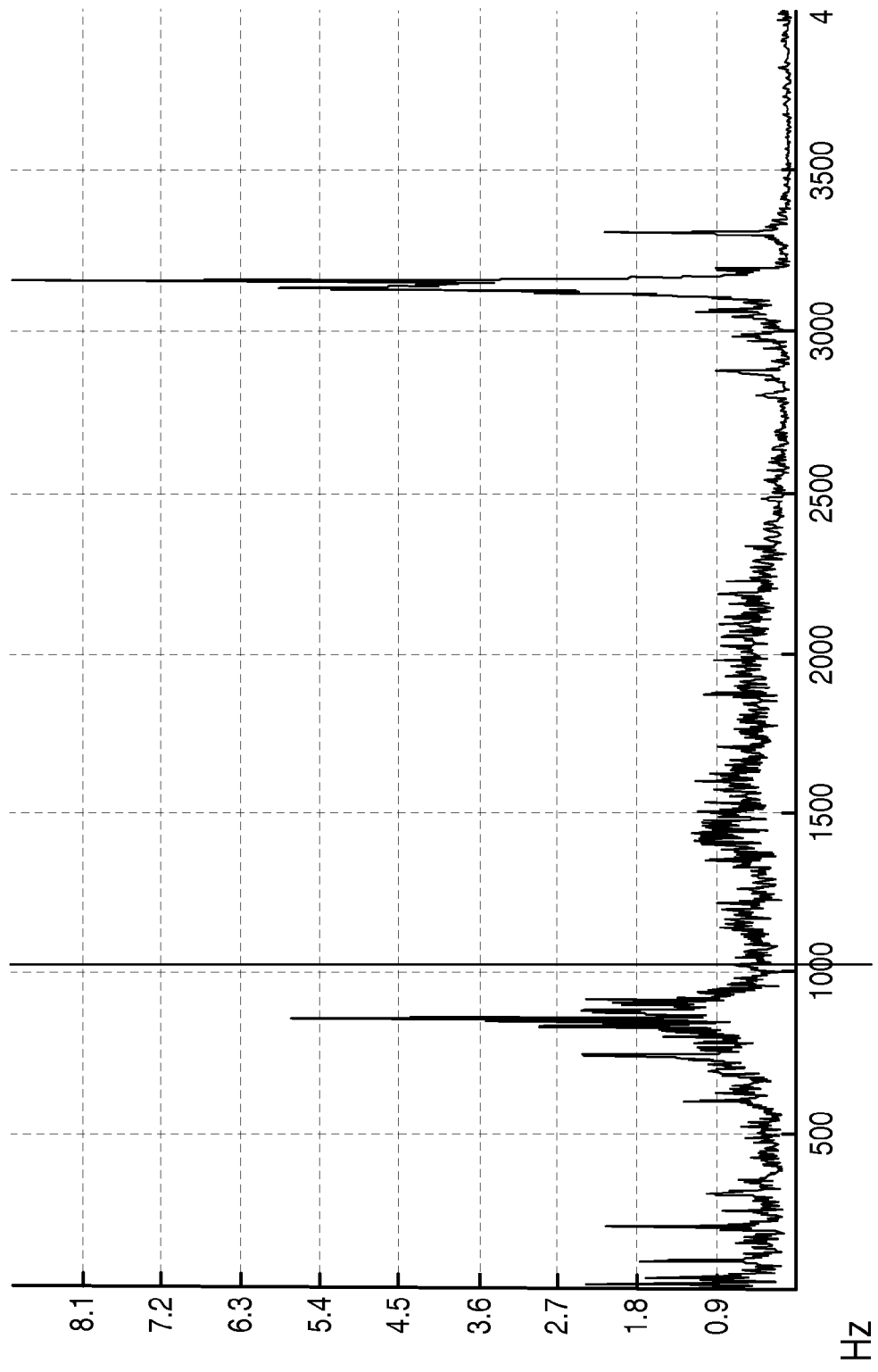
FIGS. 3 to 5 represent experimental results as discussed in the Examples.
Figure 4:
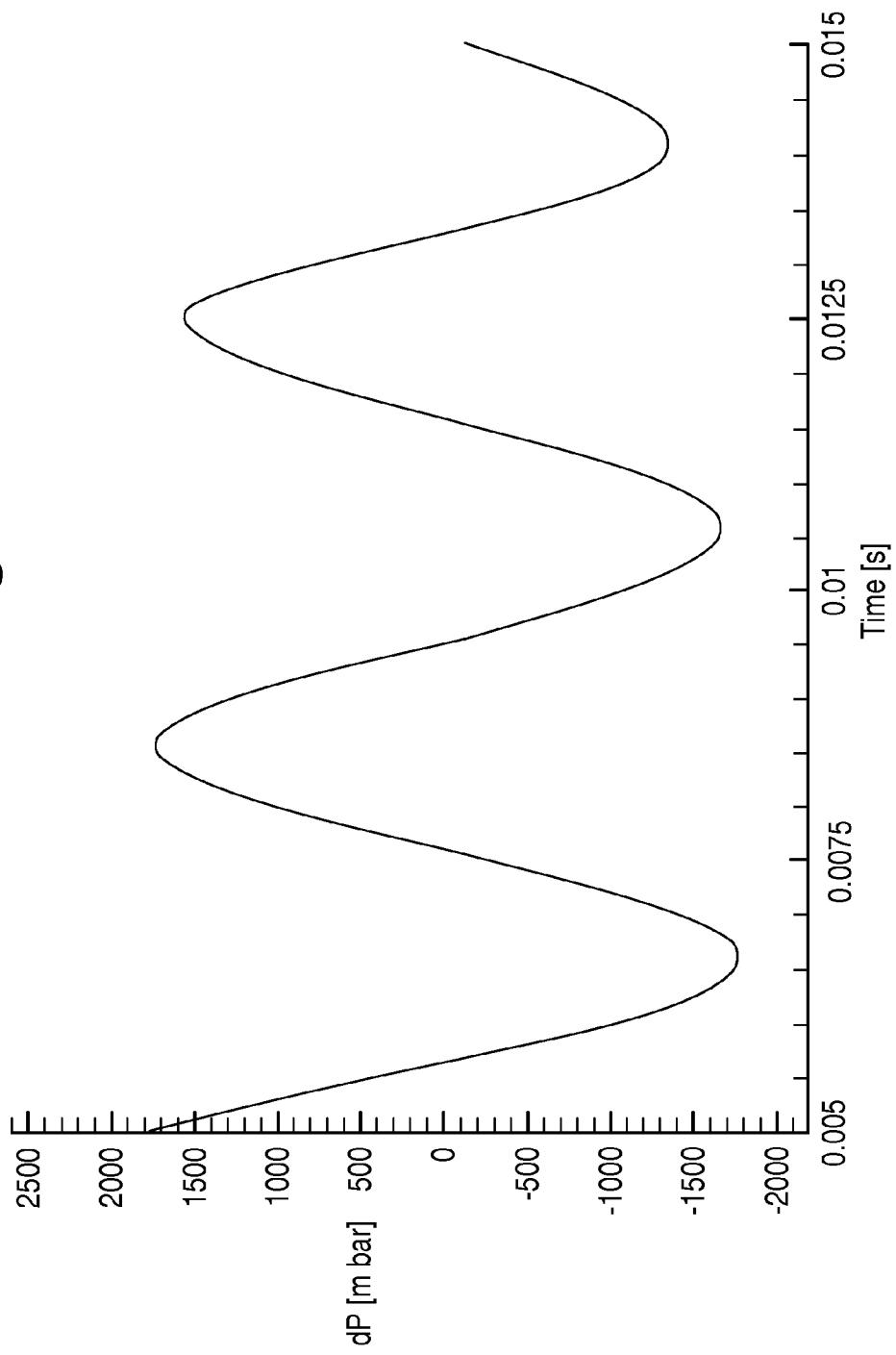

The results from the Comparative Example are shown in FIG. 3 and FIG. 4.

In particular, FIG. 3 shows the acoustic spectrum. Two bands in particular stand out at approximately 800 Hz and 3200 Hz. The 800 Hz frequency band is believed to correspond to a resonance caused by the step. Modeling of the effect of this leads to an oscillation in pressure drop, as shown in FIG. 4, of up to nearly ±2 bar (±2 kPa) downstream of the mixing zone. (The 3200 Hz frequency band is believed to be related to the resonant frequency of the linear first tube).

As well as the pressure variations in FIG. 4, the variations in the absolute (and relative) pressure drops through the nozzle and annulus may be expected to result in significant variations in the composition of the mixture of hydrocarbon and oxygen formed, including the potential to lead to rapid oscillation between fuel rich and fuel lean compositions which, as noted previously, may lead to short lived high gas temperatures or reaction extinction.

Figure 5:
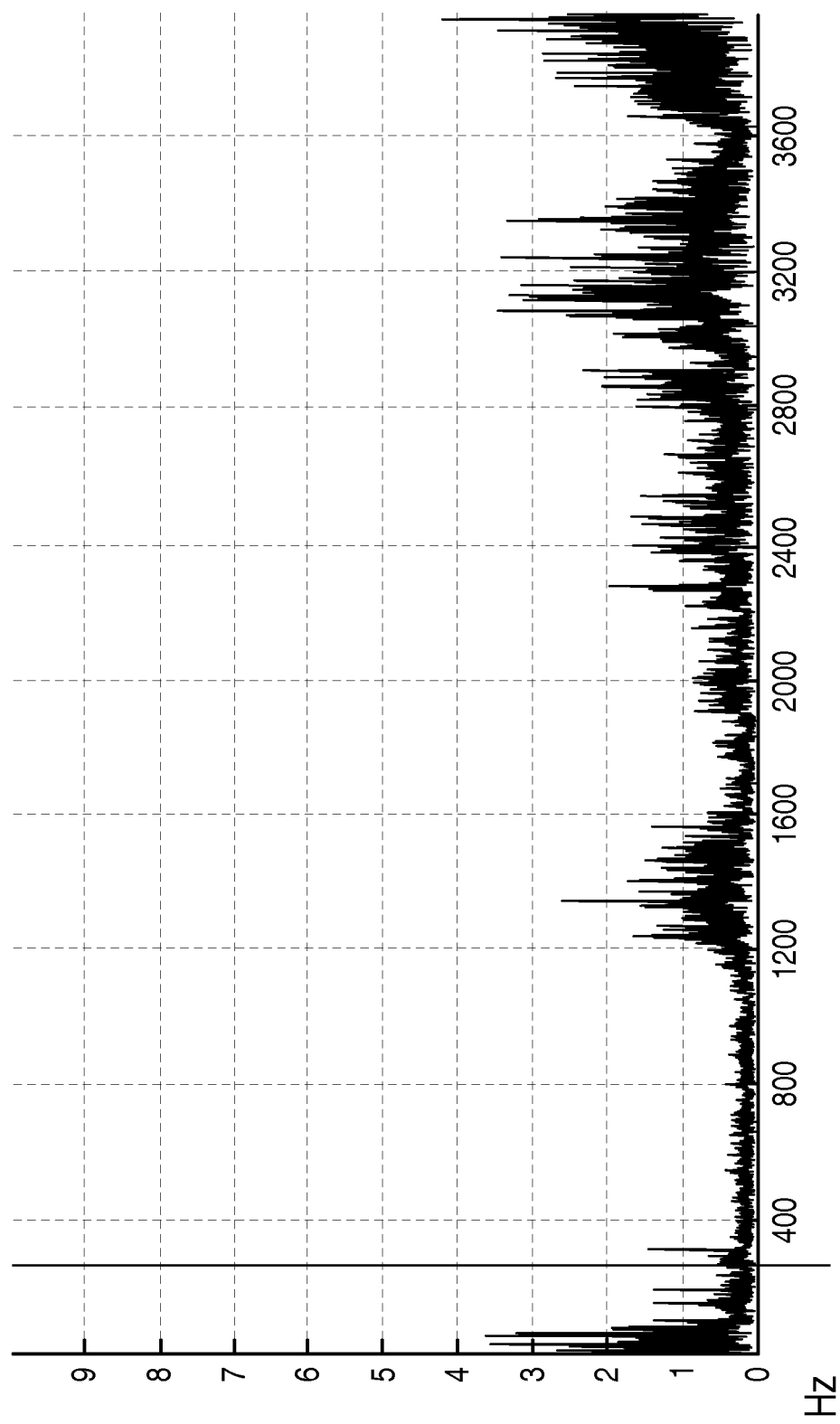

The results from Example 1 (according to the present invention) are shown in FIG. 5. It can be seen that the acoustic spectrum is much cleaner and the oscillations seen with the earlier design have disappeared. This shows that the pressure drop oscillations obtained from the Comparative Example have been avoided by the present design.

Similar results are obtained over a range of respective flow rates.

The invention claimed is:

1. A mixing apparatus for mixing a first gas and a second gas, which mixing apparatus comprises:
   i) a linear first tube for supply of the first gas, said first tube comprising an inlet for the first gas at an upstream end and tapering to form a nozzle at a downstream end, said nozzle having an opening of internal area of less than 10 mm$^2$ at the outlet for the first gas and providing a pressure drop in the supply of the first gas through said first tube, and
   ii) a linear second tube for supply of the second gas, said second tube comprising an inlet for the second gas at an upstream end, a first portion which forms an annulus around the outer surface of the first tube upstream of the nozzle, which annulus has a length of 5 to 50 mm and a cross-section area of 2 to 10 times the area of the opening of the nozzle and which acts to provide a pressure drop in the supply of the second gas through said second tube, and a second portion which forms a sheath around the nozzle of the first tube and which forms an area of expanded cross-section compared to the annulus,
   and wherein:
   a) the dimensions of the nozzle and annulus are such that the pressure drops caused in the supply of the first and second gases are in a ratio of 2:1 to 1:2,
   b) the angle of the external taper of the nozzle is less than 12° compared to the longitudinal axis of the first tube, and
   c) any change in diameter of second tube in the second portion takes place by a slope or a taper with an angle of less than 12° compared to the longitudinal axis of the second tube.

2. The mixing apparatus according to claim 1 wherein the angle of the taper of the nozzle is less than 7° compared to the longitudinal axis of the first tube and any change in diameter of the second tube in the second portion takes place by a slope or a taper with an angle of less than 7° compared to the longitudinal axis of the second tube.

3. The mixing apparatus according to claim 1 wherein the internal area of the opening of the nozzle is from 0.5 to 5.0 mm$^2$.

4. The mixing apparatus according to claim 3 wherein the internal area of the opening of the nozzle is less than the internal cross-sectional area of the linear first tube other than at the nozzle, the opening thus setting the pressure drop in the linear first tube, which pressure drop is in the range 10 to 400 kPa.

5. The mixing apparatus according to claim 1 wherein any changes in external diameter of the linear first tube take place by a slope or a taper with an angle of less than 12° compared to the longitudinal axis of the linear first tube.

6. The mixing apparatus according to claim 1 wherein the annulus is of a length of 5 to 30 mm.

7. The mixing apparatus according to claim 6 wherein the annulus has a length of 5-30 mm and the annulus cross-section is in the range 5-60 mm$^2$, the annulus setting the pressure drop in the linear second tube, which pressure drop is in the range 10 to 400 kPa.

8. The mixing apparatus according to claim 1 wherein the nozzle and annulus are arranged such that the pressure drops are in a ratio of 1:1 to 1:1.5.

9. The mixing apparatus according to claim 1 wherein upstream of the annulus, the linear second tube has a wider internal cross-section compared to the portion at the annulus, the linear second tube narrowing in the downstream direction at an angle of less than 12° to the diameter required for the annulus.

10. The mixing apparatus according to claim 1 wherein any change in the internal diameter of the linear second tube downstream of the nozzle also takes place by a slope or a taper with an angle of less than 12° compared to the longitudinal axis of the linear second tube.

11. The mixing apparatus according to claim 1 wherein the mixing apparatus comprises at least 100 linear first and second tubes.

12. A reactor for the mixing and reaction of a first gas and a second gas, which reactor comprises a mixing zone comprising the mixing apparatus as claimed in claim 1 and a reaction zone downstream of the mixing zone.

13. A process for the mixing and reaction of a first gas and a second gas, which process comprises feeding said first gas and said second gas to, respectively, one or more linear first tubes and one or more linear second tubes in a mixing apparatus as described in claim 1 and subsequently passing the gaseous mixture obtained to a reaction zone downstream of the mixing zone.

14. A process for the production of one or more olefins, said process comprising mixing an oxygen containing gas and a paraffinic hydrocarbon-containing gas by passing the oxygen-containing gas as the first gas and the paraffinic hydrocarbon-containing gas the second gas to a mixing apparatus as claimed in claim 1, passing the gaseous mixture obtained to a reaction zone via a porous resistance zone, and partially combusting in the reaction zone the gaseous mixture to produce the one or more olefins.

15. A process according to claim 14 wherein the partial combustion of the gaseous mixture in the reaction zone is carried out in the presence of a catalyst which is capable of supporting combustion beyond the fuel rich limit of flammability.

* * * * *